(12) United States Patent
Lim

(10) Patent No.: US 9,717,456 B2
(45) Date of Patent: Aug. 1, 2017

(54) VASCULAR LOCATOR DEVICE AND METHOD FOR LOCATING A VESSEL

(75) Inventor: JyueBoon Lim, New Brighton, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 207 days.

(21) Appl. No.: 14/111,395

(22) PCT Filed: Apr. 18, 2012

(86) PCT No.: PCT/US2012/034024
§ 371 (c)(1),
(2), (4) Date: Oct. 22, 2013

(87) PCT Pub. No.: WO2012/145362
PCT Pub. Date: Oct. 26, 2012

(65) Prior Publication Data
US 2014/0046217 A1   Feb. 13, 2014

Related U.S. Application Data

(60) Provisional application No. 61/476,979, filed on Apr. 19, 2011.

(51) Int. Cl.
*A61B 5/00*   (2006.01)
*A61B 17/00*   (2006.01)
*A61B 5/02*   (2006.01)
*A61B 5/107*   (2006.01)
*A61M 25/09*   (2006.01)

(52) U.S. Cl.
CPC .......... *A61B 5/489* (2013.01); *A61B 5/02007* (2013.01); *A61B 5/1076* (2013.01);
(Continued)

(58) Field of Classification Search
CPC ................ A61B 5/489; A61B 17/0057; A61B 2017/00623; A61B 2017/00672;
(Continued)

(56) References Cited

U.S. PATENT DOCUMENTS 5,951,589 A   9/1999 Epstein et al.
2008/0312683 A1   12/2008 Drasler et al.
(Continued)

FOREIGN PATENT DOCUMENTS

WO   2010081102 A2   7/2010

OTHER PUBLICATIONS

PCT International Search Report for PCT International Patent Application No. PCT/US2012/034024, mailed Jul. 11, 2012.

*Primary Examiner* — Max Hindenburg
(74) *Attorney, Agent, or Firm* — Holland & Hart

(57) ABSTRACT

A vessel locator apparatus (30) having a locator housing, and an elongated cavity defined in the locator housing, is described. The vessel locator apparatus include a superelastic wire (46) positioned at least partially in the elongated cavity, the superelastic having a proximal end and a distal end. The superelastic wire may have an elongated portion extending in a substantially longitudinal direction and a distal locator portion having an original shape configuration. The original shape configuration of distal locator portion may include a first curved segment, a second curved segment, an intermediate segment extending between the first curved segment and the second curved segment, and an end segment extending between the second curved segment and the distal end of the superelastic wire. A method of locating a vessel, such as a blood vessel, using a vessel locator apparatus is also described.

9 Claims, 8 Drawing Sheets

(52) U.S. Cl.
CPC ........ *A61B 5/6851* (2013.01); *A61B 17/0057* (2013.01); *A61M 25/0905* (2013.01); *A61B 2017/00654* (2013.01); *A61B 2017/00672* (2013.01); *A61B 2017/00867* (2013.01); *A61B 2017/00898* (2013.01)

(58) Field of Classification Search
CPC ............ A61B 2017/1205–2017/12095; A61B 17/12159; A61B 17/12109–17/12113; A61B 17/1214; A61B 17/12145; A61B 2017/00588; A61B 2017/00632; A61B 2017/00641; A61B 5/02007; A61B 5/1076; A61B 5/6851; A61B 2017/00654; A61B 2017/00898
USPC .......................... 606/191, 200, 213, 215–216
See application file for complete search history.

(56) References Cited

U.S. PATENT DOCUMENTS

| | | | | |
|---|---|---|---|---|
| 2009/0069844 | A1* | 3/2009 | Green | A61B 17/0057 606/213 |
| 2010/0179567 | A1* | 7/2010 | Voss | A61B 17/0057 606/139 |
| 2010/0228184 | A1* | 9/2010 | Mavani | A61B 17/0057 604/35 |
| 2012/0143216 | A1* | 6/2012 | Voss | A61B 17/0057 606/142 |

* cited by examiner

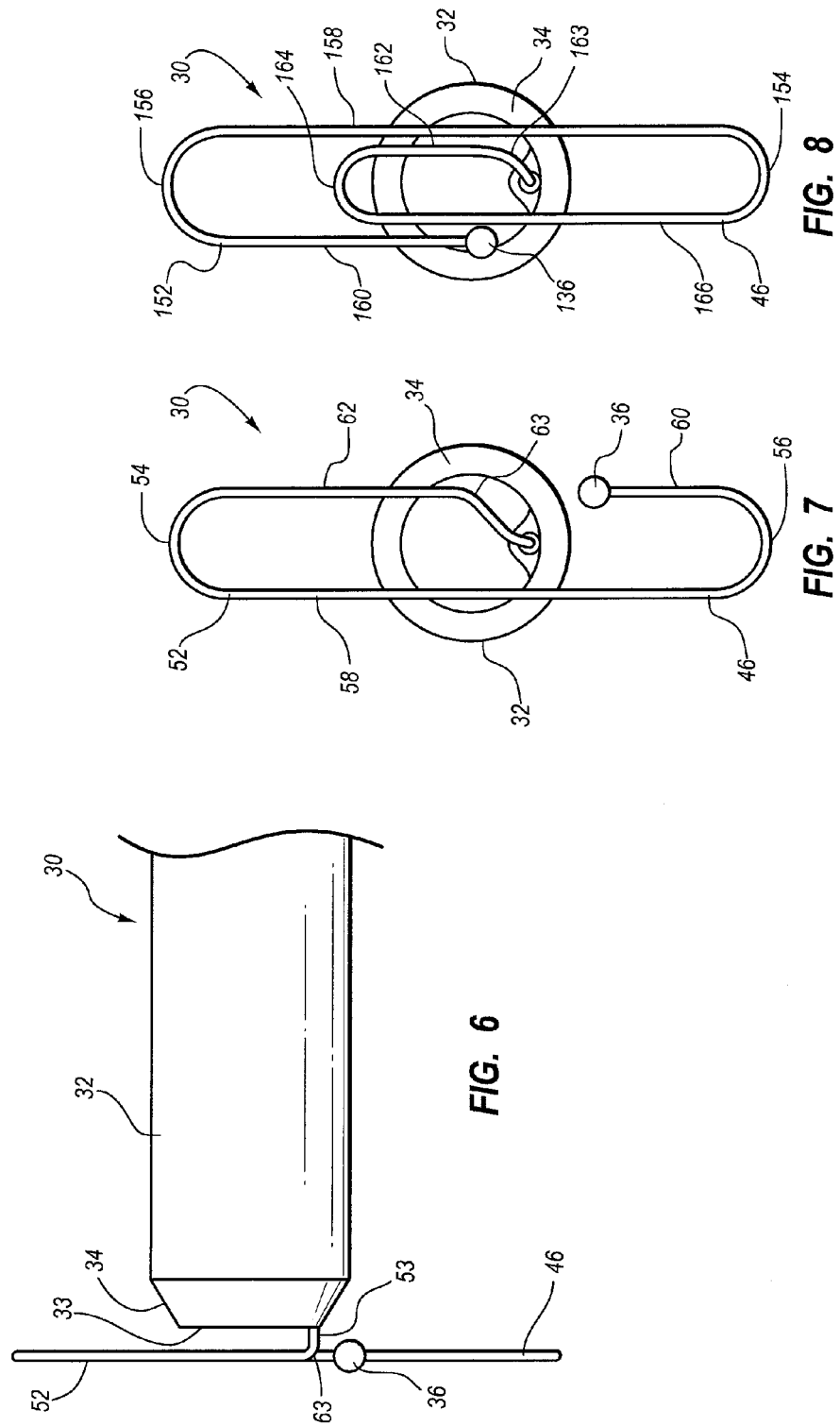

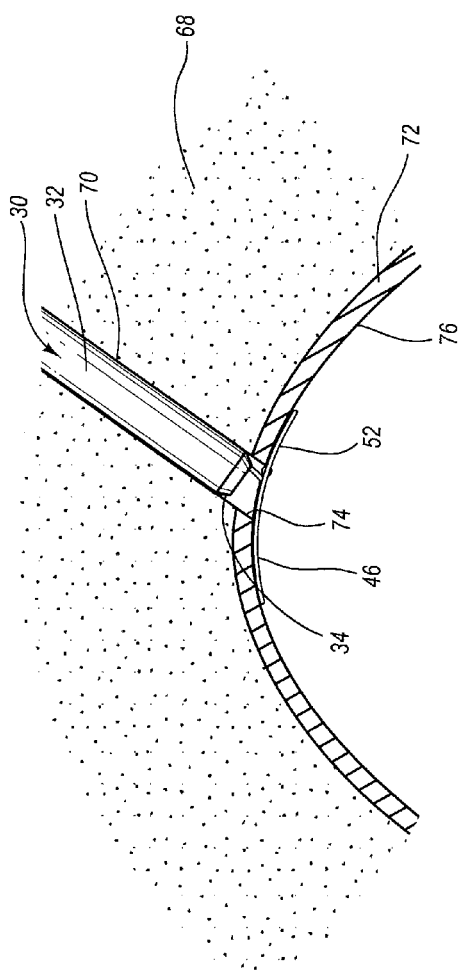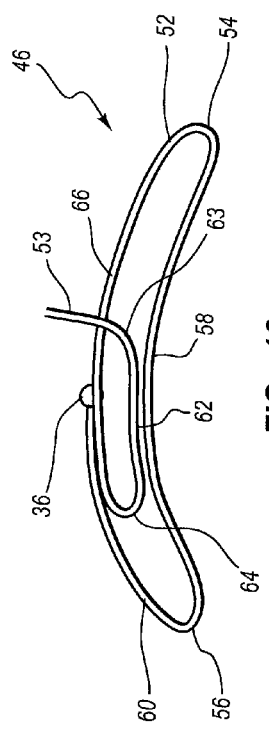

VASCULAR LOCATOR DEVICE AND METHOD FOR LOCATING A VESSEL

RELATED APPLICATION

This claims the benefit of U.S. Provisional Application No. 61/476,979, filed 19 Apr. 2011, which is hereby incorporated by reference herein its entirety. This is a national stage entry of International Application No. PCT/US2012/034024.

BACKGROUND

Catheter based diagnostic and interventional procedures such as angiograms, balloon angioplasty, stenting, atherectomy, thrombectomy, device placement, etc., are commonly employed to treat patients with various vascular obstructions or vascular related conditions accessible through the vasculature of the human body. Such interventions are often less traumatic to the body than previous surgical interventions and therefore are growing in use. The various procedures may be performed by inserting tools through a puncture site in a vessel wall, such as, for example, an arteriotomy.

Following a diagnostic or interventional procedure, a vessel puncture site may be obstructed through various means to close off the puncture site and prevent further bleeding. In certain cases, manual pressure may be applied directly to the skin above the access puncture for an extended period of time to inhibit blood loss until the body's natural clotting process seals the puncture. However, this technique may result in discomfort to the patient and may require a significant amount of hospital staff time.

Alternatively, an implant, such as a plug, may be deposited at a puncture site to obstruct the flow of blood, reducing the time and effort spent by the hospital staff in inhibiting blood flow and increasing patient comfort. In order to properly place an implant in a puncture tract, a doctor typically must first determine the location of the puncture site in the vessel wall. However, conventional locator devices may be bulky, taking up excessive space in a vascular closure instrument. Additionally, conventional locator devices may be difficult to remove after the vessel is located.

SUMMARY

According to at least one embodiment, a vessel locator apparatus may comprise a superelastic wire having a proximal end and a distal end. The superelastic wire may comprise an elongated portion extending in a substantially longitudinal direction and a distal locator portion. The distal locator portion may comprise a first curved segment, a second curved segment, an intermediate segment extending between the first curved segment and the second curved segment, and an end segment extending between the second curved segment and the distal end of the superelastic wire. Additionally, the elongated portion of the superelastic wire may extend from the distal locator portion toward the proximal end of the superelastic wire.

According to various embodiments, the distal end of the superelastic wire may comprise a rounded tip. Additionally, the intermediate segment and the end segment may be substantially parallel. The distal locator portion may further comprise a transition segment extending between the first curved segment and the elongated portion of the superelastic wire. The intermediate segment and the transition segment may also be substantially parallel. Additionally, the distal locator portion may comprise a third curved segment. According to at least one embodiment, the intermediate segment may be a first intermediate segment and the distal locator portion may further comprise a second intermediate segment extending between the first curved segment and the third curved segment of the superelastic wire. Additionally, at least two of the first curved segment, the intermediate segment, the second curved segment, and the end segment may be substantially oriented along a common plane. The elongated portion of the superelastic wire also may not be oriented along the common plane.

According to various embodiments, the first curved segment and the second curved segment may each be configured to be substantially straightened under one or more external forces and the first curved segment and the second curved segment may each be configured to return to a curved configuration upon removal of the one or more external forces. According to certain embodiments, the shape configuration of the distal locator portion may be an original shape configuration. The distal locator portion may be configured to be substantially straightened from the original shape configuration to a distorted shape configuration under one or more external forces and the distal locator portion may be configured to return to the original shape configuration upon removal of the one or more external forces. The first curved segment and the second curved segment may also be configured to be distorted in shape from the original shape configuration to a distorted shape configuration to fit within an elongated cavity having a diameter narrower than a width of the distal locator portion. The width may be measured between the intermediate segment and the end segment. According to at least one embodiment, the superelastic wire may comprise a shape memory material, including a nickel and titanium alloy. The distal locator portion may have a lateral extent greater than its longitudinal extent. The distal locator portion may also be configured to substantially conform to a shape of an interior vessel wall.

According to additional embodiments, a vessel locator apparatus may comprise a locator housing and an elongated cavity defined in the locator housing. A superelastic wire may be positioned at least partially in the elongated cavity, the superelastic wire having a proximal end and a distal end. The superelastic wire may comprise an elongated portion extending in a substantially longitudinal direction and a distal locator portion having an original shape configuration. The original shape configuration of the distal locator portion may comprise a first curved segment, a second curved segment, an intermediate segment extending between the first curved segment and the second curved segment, and an end segment extending between the second curved segment and the distal end of the superelastic wire.

According to various embodiments, the distal locator portion of the superelastic wire may be positioned within the elongated cavity and the distal locator portion may have a distorted shape configuration differing from the original shape configuration while positioned in the elongated cavity. The distal locator portion may be configured to automatically assume the original shape configuration after removal of at least part of the distal locator portion from the elongated cavity. The distal locator portion may not be folded in the elongated cavity. The distal locator portion may also be substantially straightened in the elongated cavity. The original shape configuration may be a memorized shape configuration. According to an additional embodiment, the vessel locator apparatus may further comprise an insertion sheath and the locator housing may be positioned within the insertion sheath. The vessel locator apparatus may further comprise a vascular closure implant positioned within the insertion sheath adjacent the locator housing. Additionally, the locator housing may be positioned between the insertion sheath and an exterior of the vascular closure implant.

According to various embodiments, a method of locating a vessel may comprise providing a vessel locator apparatus, the vessel locator apparatus comprising a locator housing having a distal end and a superelastic wire positioned at least partially in an elongated cavity defined in the locator housing, the superelastic wire comprising a distal locator portion positioned within the elongated cavity in an insertion shape configuration. The method may additionally comprise inserting the distal end of the locator housing into a vessel. The method may further comprise extending the distal locator portion of the superelastic wire into the vessel such that the distal locator portion is external to the distal end of the locator housing, wherein the distal locator portion assumes a deployment shape configuration. The deployment shape configuration may comprise a first curved segment, a second curved segment, an intermediate segment extending between the first curved segment and the second curved segment, and an end segment extending between the second curved segment and a distal end of the superelastic wire.

According to certain embodiments, the method of locating a vessel may further comprise positioning the vessel locator apparatus such that the distal locator portion of the superelastic wire contacts a wall of the vessel. Additionally, the distal locator portion of the superelastic wire may substantially conform to a shape of the wall of the vessel. The method of locating a vessel may further comprise retracting at least part of the distal locator portion of the superelastic wire into the locator housing.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

FIG. 6 is a side view of a distal portion of a vascular locator device according to an additional embodiment;

FIG. 7 is a front view of a distal portion of a vascular locator device according to an additional embodiment;

FIG. 8 is a front view of a distal portion of a vascular locator device according to an additional embodiment;

FIG. 12 is a side view of a vascular locator device disposed in a puncture tract according to an additional embodiment;

FIG. 13 is a perspective view of a distal portion of a locator wire according to at least on embodiment.

Figure 1:
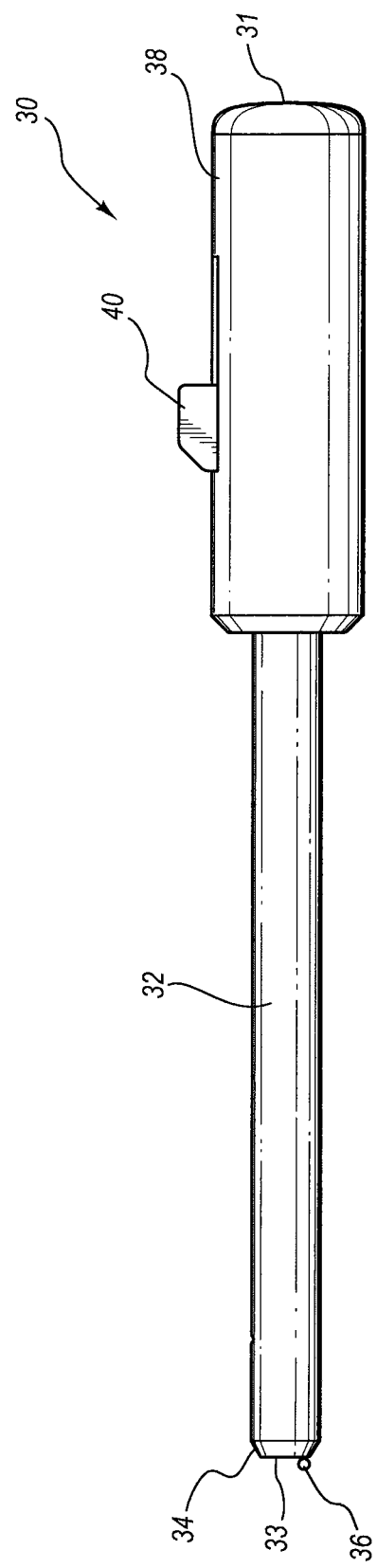
FIG. 1 is a side view of a vascular locator device according to at least one embodiment.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION OF EXEMPLARY EMBODIMENTS

A number of embodiments of vascular locator devices are shown and described herein. In various embodiments, the vascular locator devices may be used to locate the site of a hole or puncture in a blood vessel such as an arteriotomy. In additional embodiments, the vascular locator devices may be used in conjunction with vascular closure devices configured to deploy one or more vascular closure implants in a puncture tract at and/or adjacent to a vessel puncture site for the purposes of controlling and/or preventing bleeding from the vessel. According at least one embodiment, the vascular locator devices may be formed integrally with a vascular closure device.

FIG. 1 is an exemplary vascular locator device 30 according to at least one embodiment. As illustrated in this figure, vascular locator device 30 may comprise an insertion sheath 32, an end portion 34, a distal wire tip 36, a device handle 38, and a button 40. As additionally illustrated in FIG. 1, vascular locator device 30 may comprise a proximal end 31 and a distal end 33.

As used in this application, a "proximal direction" may refer to a direction generally facing toward proximal end 31 of vascular locator device 30, and a "distal direction" may refer to a direction generally facing toward distal end 33 of vascular locator device 30. Proximal end 31 of vascular locator device 30 may include an end portion of vascular locator device 30 that is located in relatively closest proximity to an operator of vascular locator device 30 when vascular locator device 30 is in use (e.g., an end portion of device handle 38 of vascular locator device 30). Additionally, distal end 33 of vascular locator device 30 device may include an end portion of vascular locator device 30 that is located in relatively closest proximity to the site of a puncture tract when vascular locator device 30 is in use. (e.g., an end portion of insertion sheath 32 of vascular locator device 30).

Distal wire tip 36 may comprise an end portion of a locator wire 46, as will be explained in greater detail below with reference to FIG. 4. Insertion sheath 32 may comprise a portion of vascular locator device 30 configured to be inserted into a puncture tract and/or a vessel puncture opening prior to deployment of a locator wire in a vessel.

Insertion sheath 32 may also comprise a sheath end portion 34. Sheath end portion 34 may include an end portion of insertion sheath 32 that slopes from a narrower diameter at distal end 33 of vascular locator device 30 to a wider diameter at a point located proximally from distal end 33. Sheath end portion 34 may be configured to aid in insertion of insertion sheath 32 into a puncture tract, expanding the puncture tract to accommodate insertion sheath 32. According to additional embodiments, insertion sheath 32 may also comprise one or more blood inlet holes defined in insertion sheath 32 (see, e.g., blood inlet hole 42 in FIGS. 2 and 4).

Device handle 38 may comprise a portion of vascular locator device 30 formed to any shape and size suitable to allow a user to grasp and operate vascular locator device 30. Device handle 38 may comprise one or more buttons, switches, and/or other suitable mechanisms suitable for enabling a user to operate vascular locator device 30. For example, device handle 38 may comprise a button 40 configured to at least partially operate vascular locator device.

Figure 2:
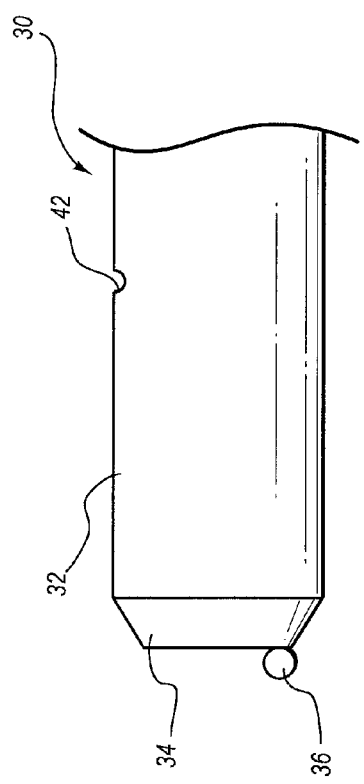
FIG. 2 is a side view of a distal portion of a vascular locator device according to at least one embodiment.
Figure 3:
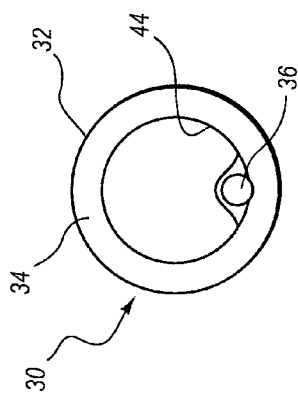
FIG. 3 is a front view of a distal portion of a vascular locator device according to an additional embodiment.

FIGS. 2 and 3 show a side view and a front view respectively of a distal end portion of an exemplary vascular locator device 30 according to at least one embodiment. As illustrated in these figures, vascular locator device 30 may comprise an insertion sheath 32 and a distal wire tip 36. Insertion sheath 32 may comprise a portion of vascular locator device 30 configured to be inserted into a puncture tract and/or a vessel puncture opening prior to deployment of vascular locator device 30. Additionally, insertion sheath 32 may comprise a blood inlet hole 42 and a sheath end portion 34. According to various embodiments, blood inlet hole 42 may be in fluid communication with a lumen extending through a portion of vascular locator device 30, and the lumen may in turn be in fluid communication with a blood outlet hole and/or a blood indicator. According to at least one embodiment, blood inlet hole 42 may be used to determine an insertion depth of insertion sheath 32 into a blood vessel and/or to signal over-insertion, under-insertion, and/or proper insertion of insertion sheath 32 into the blood vessel during a procedure.

Figure 4:
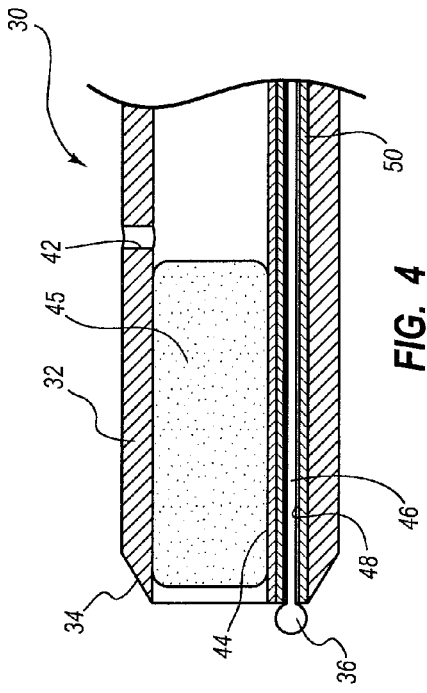
FIG. 4 is a cross-sectional view of a distal portion of a vascular locator device according to an additional embodiment.

In additional embodiments, as illustrated in FIGS. 3 and 4, vascular locator device 30 may comprise an insertion sheath cavity 44 defined by and formed within insertion sheath 32. According to various embodiments, insertion sheath cavity 44 may be formed in a vascular locator device 30 that is formed integrally with a vascular closure device configured to hold and/or protect a vascular closure implant 45 prior to deployment of vascular closure implant 45. For example, insertion sheath 32 may aid in introducing vascular closure implant 45 into a puncture tract and/or a vessel puncture site.

Vascular closure implant 45 may be formed in any suitable shape configuration and may comprise any suitable material or combination of materials, without limitation. In at least one embodiment, vascular closure implant 45 may comprise an absorbent material that may swell and/or expand when introduced into a puncture tract. Such materials may include, without limitation, collagen materials and/or other protein-based materials. Collagen materials may swell and/or expand in the presence of various fluids such as, for example, fluids present in blood. A material such as collagen may exert various forces on a puncture tract and/or a vessel puncture site based on the geometry of vascular closure implant 45. Additionally, a material such as collagen may exert various forces on a puncture tract and/or a vessel puncture site due to the swelling and/or expanding of the vascular closure implant 45.

In at least one embodiment, vascular closure implant 45 may be positioned inside insertion sheath cavity 44 prior to insertion of insertion sheath 32 into a puncture tract. Subsequently, insertion sheath 32 may be inserted into a puncture tract. During insertion of insertion sheath 32 into a puncture tract, insertion sheath 32 may assist in guiding and/or positioning vascular closure implant 45 prior to deployment of vascular closure implant 45 in a puncture tract. Additionally, insertion sheath 32 may assist in protecting vascular closure implant 45 and/or may prevent or reduce the amount of liquid contacting vascular closure implant 45 prior to deployment of vascular closure implant 45 in a puncture tract.

FIG. 4 is a cross-sectional side view of the distal end portion of the exemplary vascular locator device 30 illustrated in FIGS. 2 and 3 according to an additional embodiment. As illustrated in FIG. 4, vascular locator device 30 may comprise an insertion sheath 32 and an insertion sheath cavity 44 defined by one or more interior surfaces within insertion sheath 32. Vascular locator device 30 may also comprise a locator wire 46 disposed within at least a portion of insertion sheath 32. At least a portion of locator wire 46 may comprise a vessel locator portion (see, e.g., distal locator portion 52 in FIG. 5) configured to identify at least a portion of a vessel and/or configured to hold vascular locator device in position for deployment of vascular closure implant 45 in an implant tract and/or vessel puncture opening. Locator wire 46 may be positioned within any suitable portion of insertion sheath 32. For example, locator wire 46 may be disposed within a locator passage 48, as illustrated in FIG. 4.

Locator passage 48 may comprise an elongated cavity or passageway formed and/or defined within insertion sheath 32. In certain embodiments, locator passage 48 may be integrally formed with insertion sheath 32. In additional embodiments, locator passage 48 may be defined within a locator housing 50 disposed within at least a portion of insertion sheath 32 and/or insertion sheath cavity 44. For example, locator housing 50 may comprise a generally tubular member disposed within insertion sheath 32. Locator wire 46 may also be disposed within insertion sheath 32 at a position radially outward from a longitudinal axis of insertion sheath cavity 44. In additional embodiments, locator wire 46 may be disposed within any suitable portion of insertion sheath cavity 44, such as for example, at or near a longitudinal axis of insertion sheath cavity 44.

As shown in FIGS. 3 and 4, locator housing 50, locator passage 48, and/or locator wire 46 may take up a relatively small area in comparison with insertion sheath cavity 44. Additionally, locator housing 50, locator passage 48, and/or locator wire 46 may be disposed to the side of insertion sheath cavity 44, allowing maximization of the space available in insertion sheath cavity 44. Accordingly, vascular closure implant 45 may be relatively easily disposed within and removed from insertion sheath cavity 44 without interference from locator housing 50, locator passage 48, and/or locator wire 46.

Locator wire 46 may comprise an elongated member, such as, for example, a wire, a rod, a fiber, or a filament, formed of any material suitable for insertion into a blood vessel for purposes of locating at least a portion of the vessel and/or for positioning vascular closure implant 45 within puncture tract through and/or adjacent to the vessel. Additionally, locator wire 46 may be formed to any suitable size or shape. For example, locator wire 46 may comprise a relatively thin wire having a diameter within a range of about 0.02 inches (0.51 mm) to about 0.05 inches (1.27 mm).

In at least one embodiment, locator wire 46 may be positioned within insertion sheath 32 in a generally parallel orientation relative to a lengthwise axis of vascular locator device 30. According to various embodiments, locator wire 46 may be positioned in locator passage 48 such that locator wire 46 is generally straightened, although locator wire may also have a slightly meandering configuration within locator passage 48, such as in a case where locator passage 48 has a larger diameter than locator wire 46. Accordingly, locator wire 46 may be substantially straightened such that it may be positioned in locator passage 48 in a lengthwise, non-overlapping manner, while maintaining a slightly meandering or undulating configuration within locator passage 48. According to certain embodiments, a proximal section of locator wire 46 may be located outside of locator passage 48 and may assume any suitable shape configuration, including a straightened, curved, and/or bent configuration.

In at least one embodiment, locator wire 46 may comprise a superelastic and/or a shape memory material having superelastic and/or shape memory characteristics, and may include, for instance, a metallic and/or a polymer material. In various embodiments, locator wire 46 may comprise an elongated member, such as a wire, formed of a superelastic and/or a shape memory alloy. A suitable superelastic and/or shape memory alloy may include, without limitation, a nickel and titanium alloy, such as, for example, a Nitinol alloy.

According to at least one embodiment, a superelastic and/or shape memory material may include a material capable of being substantially deformed from an original shape and/or a memorized shape, substantially returning to the original shape at a later time. For example, a portion of locator wire 46 comprising a superelastic and/or shape memory material may be formed to an original shape having a specific crystallographic configuration through any suitable means. Subsequently, the portion of locator wire 46 comprising a superelastic and/or shape memory material may be deformed from the original shape to a distorted shape under various conditions, loads, and/or stresses. The portion of locator wire 46 comprising a superelastic and/or shape memory material may later automatically return to a shape substantially equivalent to the original shape under various conditions, such as when a stress and/or load maintaining the portion of locator wire 46 in the distorted shape is removed from the portion of locator wire 46. According to additional embodiments, locator wire 46 may return to an original and/or memorized shape upon a change in temperature, such as, for example, an increase in temperature.

In at least one embodiment, at least a portion of locator wire 46 may be formed into an original and/or memorized shape prior to disposing locator wire 46 within at least a portion of insertion sheath 32. As will be described in greater detail below, a portion of locator wire 46 may be formed to any original shape suitable for use in locating at least a portion of a vessel and/or for positioning vascular closure implant 45 within puncture tract 70. Locator wire 46 may retain shape memory of the original shape, even after being substantially distorted.

Following formation of at least a portion of locator wire 46 to an original shape and/or memorized shape, locator wire 46 may be formed to a distorted shape that is different from the original shape. For example, locator wire 46 may be formed to any distorted shape suitable for placing and/or fitting locator wire 46 within insertion sheath 32 and/or locator passage 48. For example, locator wire 46 may be substantially straightened within locator passage 48 under one or more external forces. Walls of locator passage 48 may maintain locator wire 46 in a distorted shape. Additionally, locator wire 46 may be formed to any distorted shape suitable for deploying locator wire 46 from vascular locator device 30 into a vessel and/or a puncture tract.

Locator wire 46 may also comprise a distal wire tip 36. Distal wire tip 36 may be formed, for example, by crimping and/or melting an end portion of locator wire 46. In certain embodiments, a separate material may be adhered to an end portion of locator wire 46 to form distal wire tip 36. Distal wire tip 36 may be formed to any shape and size suitable for enabling atraumatic introduction and deployment of locator wire 46 into a vessel and/or puncture tract. In at least one embodiment, distal wire tip 36 may comprise a rounded end portion of locator wire 46.

Figure 5:
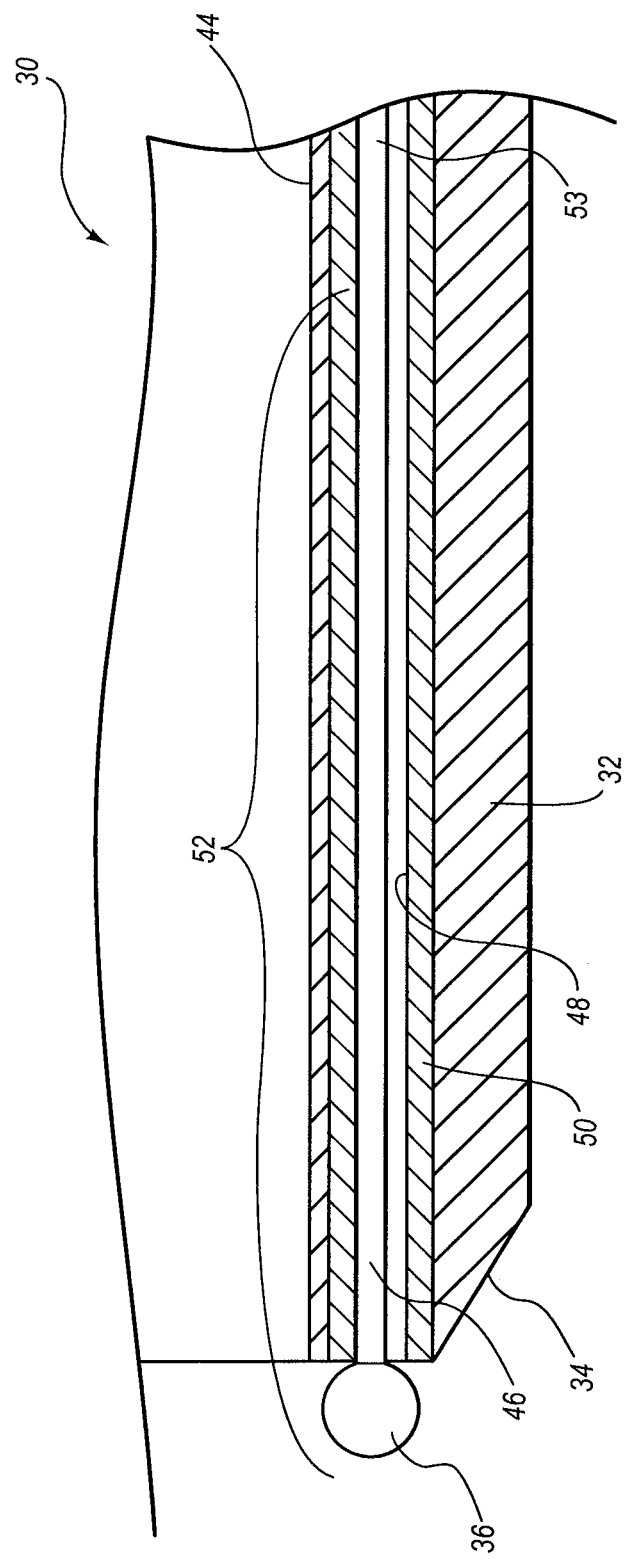
FIG. 5 is a cross-sectional view of a distal portion of a vascular locator device according to an additional embodiment.

FIG. 5 is a cross-sectional view of a distal end portion of an exemplary vascular locator device 30 according to an additional embodiment. As illustrated in this figure, locator wire 46 may be disposed within a locator housing 50 within insertion sheath 32. In various embodiments, locator housing 50 may comprise any suitable material, and may comprise any shape or size suitable for holding and/or deploying locator wire 46. According to additional embodiments, locator housing 50 may be positioned within at least a portion of insertion sheath 32 between insertion sheath 32 and insertion sheath cavity 44. Locator housing 50 may also be positioned within insertion sheath cavity 44. In additional embodiments, locator housing 50 may be positioned substantially centrally within at least a portion of insertion sheath cavity 44, such as, for example, at or near a central axis extending through insertion sheath cavity 44. In various embodiments, locator housing 50 and insertion sheath 32 may be capable of moving relative to one another, such as, for example, during deployment of locator wire 46 and/or a vascular closure implant (see, e.g., vascular closure implant 45 in FIG. 4).

FIGS. 6-8 show a side view and front views, respectively, of a distal end portion of an exemplary vascular locator device 30 in which distal locator portion 52 of locator wire 46 is in an expanded configuration outside of insertion sheath 32, according to at least one embodiment. As illustrated in these figures, locator wire 46 may comprise a distal locator portion 52 extending from distal end 33 of vascular locator device 30, distal locator portion 52 being deployed in an expanded configuration.

The expanded configuration of distal locator portion 52 illustrated in FIGS. 6-8 may be an original and/or deployment shape configuration of distal locator portion 52 of locator wire 46 or a shape configuration that is relatively and/or substantially equivalent to the original shape configuration of distal locator portion 52. For example, distal locator portion 52 of locator wire 46 may be formed to an original shape configuration, following which distal locator portion 52 of locator wire 46 may be distorted when it is positioned in insertion sheath cavity 44 within insertion sheath 32 and/or locator housing 50.

In at least one embodiment, locator wire 46, including distal locator portion 52, may be straightened and/or distorted to a generally elongated shape within insertion sheath 32 and/or locator housing 50. The shape of distal locator portion 52 while it is positioned within insertion sheath 32 and/or locator housing 50 may also be referred to as an insertion shape configuration. Subsequently, locator wire 46 may be deployed to locate at least a portion of a vessel and/or at least a portion of a puncture tract. During deployment of locator wire 46, at least a portion of distal locator portion 52 may be displaced from insertion sheath 32 and/or locator housing 50 at or near distal end 33. A part of distal locator portion 52 of locator wire 46 protruding from insertion sheath 32 and/or locator housing 50 may substantially return to an original shape configuration, as illustrated in FIGS. 6-8. The shape of distal locator portion 52 while it is positioned external to insertion sheath 32 and/or locator housing 50 may also be referred to as a deployment shape configuration.

Distal locator portion 52 of locator wire 46 may be formed to an original shape configuration having any shape or size suitable for use in locating at least a portion of a vessel and/or at least a portion of a puncture tract. In at least one embodiment, distal locator portion 52 may have a shape that prevents distal locator portion 52 from passing through a vessel puncture opening 74 in vessel 72. Additionally, distal locator portion 52 may be longer and/or wider than a width and/or diameter of insertion sheath 32.

FIGS. 6-8 illustrate various original and/or deployment shape configurations of distal locator portion 52. As illustrated in FIG. 6, locator wire 46 may comprise an elongated portion 53, a part of which is visible extending beyond distal end 33 of insertion sheath 32 and the remainder of which remains within insertion sheath 32 and or device handle 38. According to at least one embodiment, elongated portion 53 of locator wire 46 may extend in a distal direction to device handle 38 (see, e.g., FIG. 1) where locator wire 46 may be directly and/or indirectly controlled by a user. Locator wire 46 may additionally comprise a curved portion 63, where locator wire 46 transitions between elongated portion 53 and distal locator portion 52. In various embodiments, curved portion 63 may curve gradually and/or abruptly between elongated portion 53 and distal locator portion 52, and curved portion 63 may comprise one or more curved sections of locator wire 46.

According to various embodiments, as illustrated in FIG. 7, distal locator portion 52 of locator wire 46 may comprise a first curved segment 54 and a second curved segment 56. Distal locator portion 52 may additionally comprise a first intermediate segment 58 extending between first curved segment 54 and second curved segment 56. Distal locator portion 52 may further comprise an end segment 60 extending between second curved segment 56 and distal wire tip 36. In addition, distal locator portion 52 may comprise a transition segment 62 extending between first curved segment 54 and curved portion 63 and/or elongated portion 53 of locator wire 46.

In at least one embodiment, as illustrated in FIG. 7, first intermediate segment 58 and end segment 60 may be oriented generally or substantially parallel to each other, along at least a portion of their lengths. Similarly, first intermediate segment 58 and transition segment 62 may be oriented generally or substantially parallel to each other, along at least a portion of their lengths. According to certain embodiments, a section of locator wire 46 comprising first curved segment 54 and/or a section of locator wire 46 comprising second curved segment 56 may be formed to an arc or generally arcuate shape of approximately 180 degrees.

According to at least one embodiment, distal locator portion 52 of locator wire 46 may be formed to a shape configuration that may readily conform to an interior of a vessel, such as an artery or a vein. As shown in FIG. 7, a length of distal locator portion 52 may be greater than a width of distal locator portion 52 in order to facilitate adaptation of distal locator portion 52 to a vessel, and additionally, to prevent movement or rotation of distal locator portion 52 relative to the vessel. A width of distal locator portion 52 may be measured between first intermediate segment 58 and end segment 60. According to an additional embodiment, a width of distal locator portion 52 may be measured between first intermediate segment 58 and transition segment 62. A length of distal locator portion 52 may be measured between part of first curved segment 54 and part of second curved segment 56. In various embodiments, distal locator portion 52 may be configured to lie in a lengthwise orientation that is generally or substantially parallel to a lengthwise section of a vessel adjacent distal locator portion 52.

According to additional embodiments, distal locator portion 52 may have a lateral extent greater than its longitudinal extent. In other words, as shown in FIG. 6, distal locator portion 52 may extend more in a lateral direction than in a longitudinal direction relative to insertion sheath 32. Distal locator portion 52 may also have a length wider than a width of insertion sheath 32, such as a width of a distal portion of insertion sheath 32, as illustrated in FIGS. 6-8. Accordingly, distal locator portion 52 may extend in a lateral direction past an outer diameter of insertion sheath 32.

According to certain embodiments, as illustrated in FIG. 6, distal locator portion 52 of locator wire 46 may have a generally or substantially flattened profile when distal locator portion 52 is in deployment configuration. For example, two or more of first curved segment 54, second curved segment 56, first intermediate segment 58, end segment 60, and transition segment 62 may be generally or substantially oriented in a common plane. Additionally, elongated portion 53 of locator wire 46 may be oriented such that it is non-parallel with the common plane. According to additional embodiments, distal locator portion 52 of locator wire 46 may comprise a generally non-planar profile.

Distal locator portion 52 of locator wire 46 may be configured to enable a user of vascular locator apparatus 30 to locate a site at or near a vessel opening, such as a vessel puncture opening in an vascular vessel. Retracting distal locator portion 52 substantially into an interior of insertion sheath 32 into an insertion shape configuration prior to insertion of vascular locator apparatus 30 into a puncture tract may enable non-traumatic insertion of vascular locator apparatus 30, including at least a portion of locator wire 46, into the puncture tract. In various embodiments, distal wire tip 36, which has a substantially spherically round surface, may protrude at least partially from insertion sheath 32 during insertion into the puncture tract. Various means, such as, for example, blood inlet hole 42 (see, e.g., FIGS. 2 and 4), may be used to indicate that insertion sheath 32 has been inserted into the vessel to a depth suitable for deployment of locator wire 46 in the vessel.

Following insertion of insertion sheath 32 into a puncture tract, distal end 33 of vascular locator device 30 may extend at least partially into an interior of the vessel. A distal portion of locator wire 46, including distal locator portion 52, may be at least partially removed from a distal portion of insertion sheath 32 and/or locator housing 50 such that distal locator portion 52 extends into the vessel. Distal locator portion 52 may be at least partially removed from insertion sheath 32 using any suitable method, including, for example, by moving locator wire 46 in a distal direction relative to insertion sheath 32 using a button (see, e.g., button 40 in FIG. 1) or other control mechanism located on vascular locator device 30. Upon removal from insertion sheath 32 and/or locator housing 50, distal locator portion 52 may assume a deployment shape configuration, which may be the same as or substantially similar to the original shape configuration of distal locator portion 52. According to various embodiments, distal locator portion 52 may automatically assume the original shape configuration and/or deployment shape configuration upon removal of at least part of distal locator portion 52 from insertion sheath 32 and/or locator passage 48 defined in locator housing 50.

First curved segment 54 and/or second curved segment 56 may be curved and shaped such that distal locator portion 52 may be deployed into a vessel without causing damage to a wall of the vessel and/or tissue surrounding the vessel. Accordingly, the rounded profile of first curved segment 54 and/or second curved segment 56 may prevent damage to a portion of a vessel or other tissue contacting distal locator portion 52. After a vessel has been located using locator wire 46, distal locator portion 52 may be at least partially retracted into insertion sheath 32, and vascular locator device 30 may subsequently be removed from puncture tract 70.

According to an additional embodiment, as illustrated in FIG. 8, locator wire 46 may comprise a distal locator portion 152. Distal locator portion 152 may comprise a first curved segment 154, a second curved segment 156, and a third curved segment 164. Distal locator portion 152 may additionally comprise a first intermediate segment 158 extending between first curved segment 154 and second curved segment 156. Distal locator portion 152 may also comprise a second intermediate segment 166 extending between first curved segment 154 and third curved segment 164. Distal locator portion 152 may further comprise an end segment 160 extending between second curved segment 156 and distal wire tip 136. In addition, distal locator portion 152 may comprise a transition segment 162 extending between first curved segment 154 and curved portion 63 and/or elongated portion 53 of locator wire 46.

In at least one embodiment, as illustrated in FIG. 8, two or more of first intermediate segment 158, second intermediate segment 166, transition segment 162, and end segment 160 of distal locator portion 152 may be oriented generally or substantially parallel to each other, at least along a portion of their lengths. According to various embodiments, distal locator portion 152 may comprise any suitable number of curved segments in addition to first curved segment 154, second curved segment 156, and third curved segment 164. Distal locator portion 152 may also comprise any suitable number of intermediate segments extending between various curved segments, the intermediate segments being in addition to first intermediate segment 158 and second intermediate segment 166.

Additionally, distal locator portion 152 of locator wire 46 may have a generally or substantially flattened profile when distal locator portion 152 is in deployment configuration. For example, two or more of first curved segment 154, second curved segment 156, first intermediate segment 158, second intermediate segment 166, end segment 160, and transition segment 162 may be generally or substantially oriented in a common plane. Additionally, elongated portion 53 of locator wire 46 may be oriented such that it is non-parallel with the common plane. According to various embodiments, distal locator portion 152 of locator wire 46 may comprise a generally non-planar profile.

Figure 9:
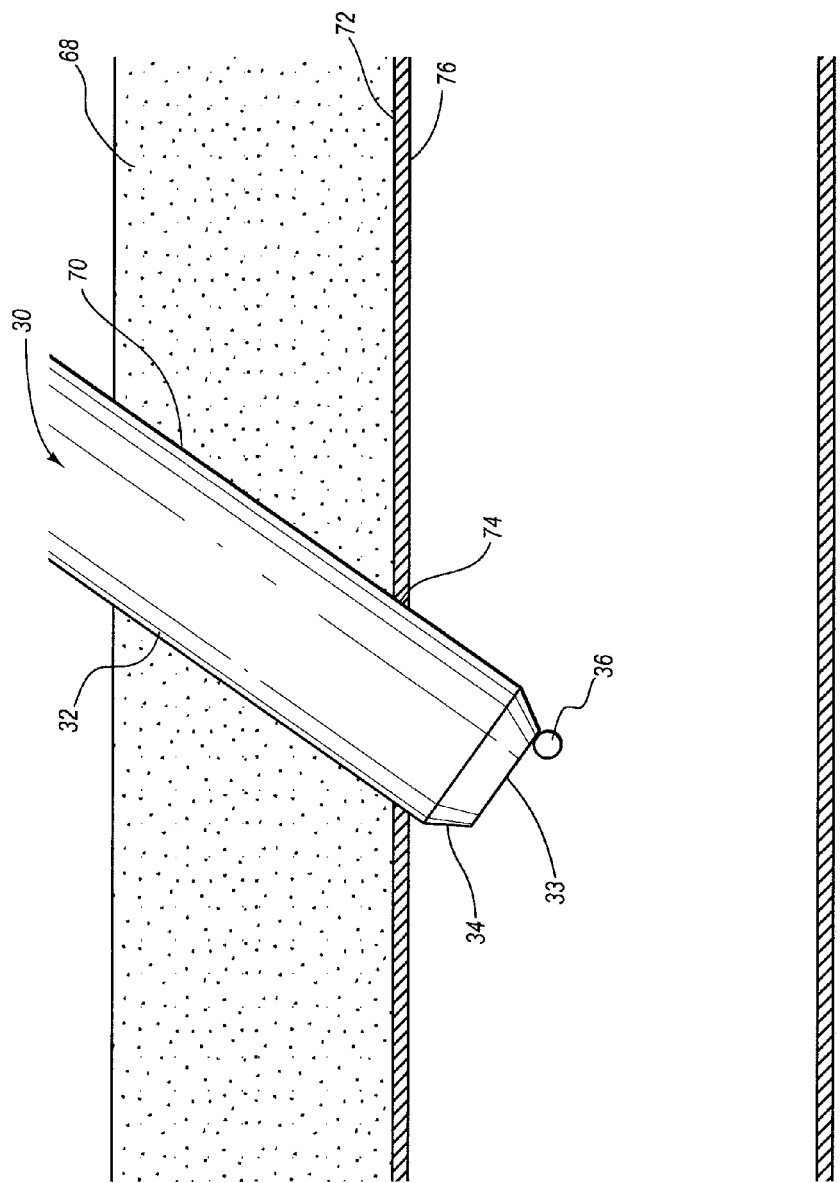
FIG. 9 is a side view of a vascular locator device disposed in a puncture tract according to at least one embodiment.
Figure 10:
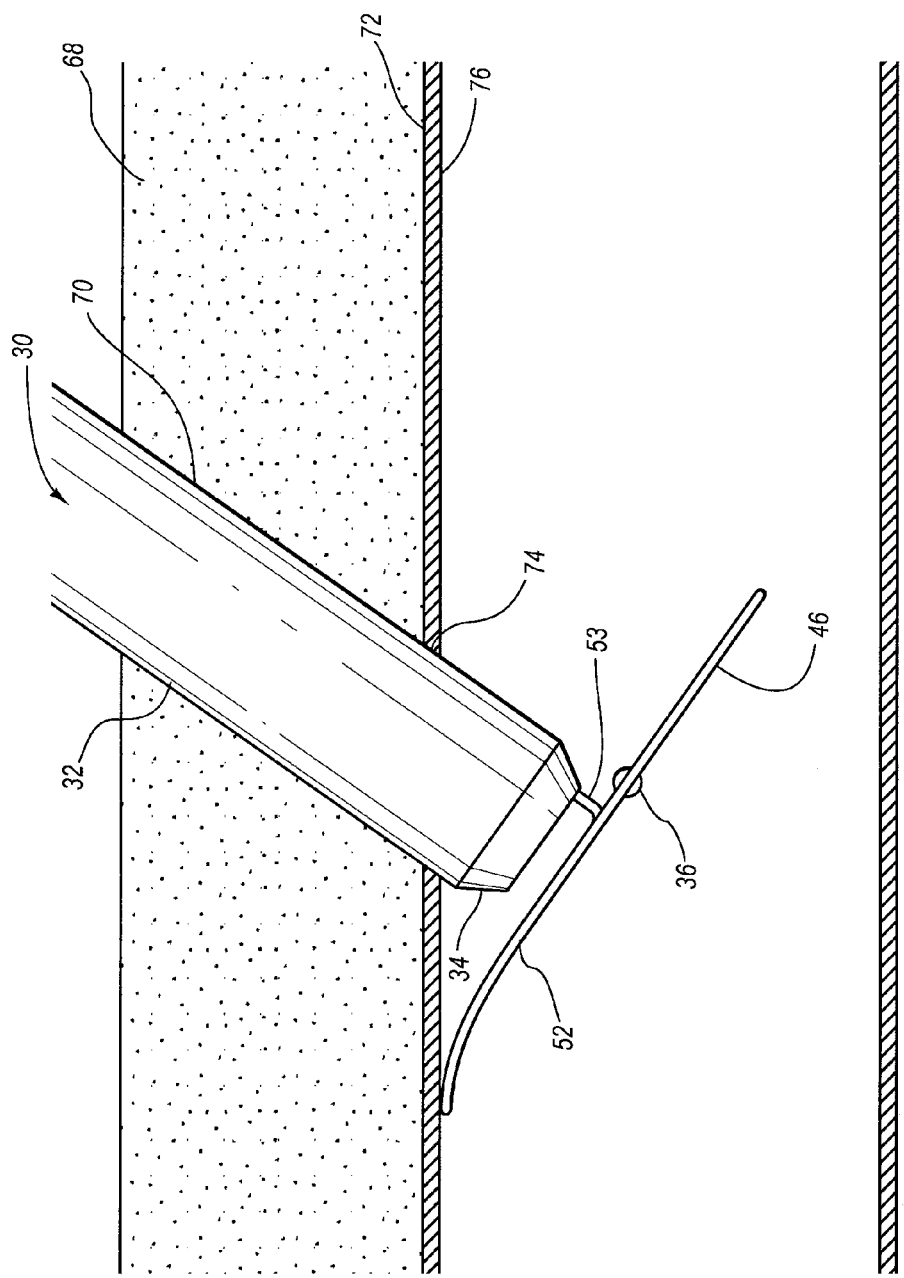
FIG. 10 is a side view of a vascular locator device disposed in a puncture tract according to an additional embodiment.
Figure 11:
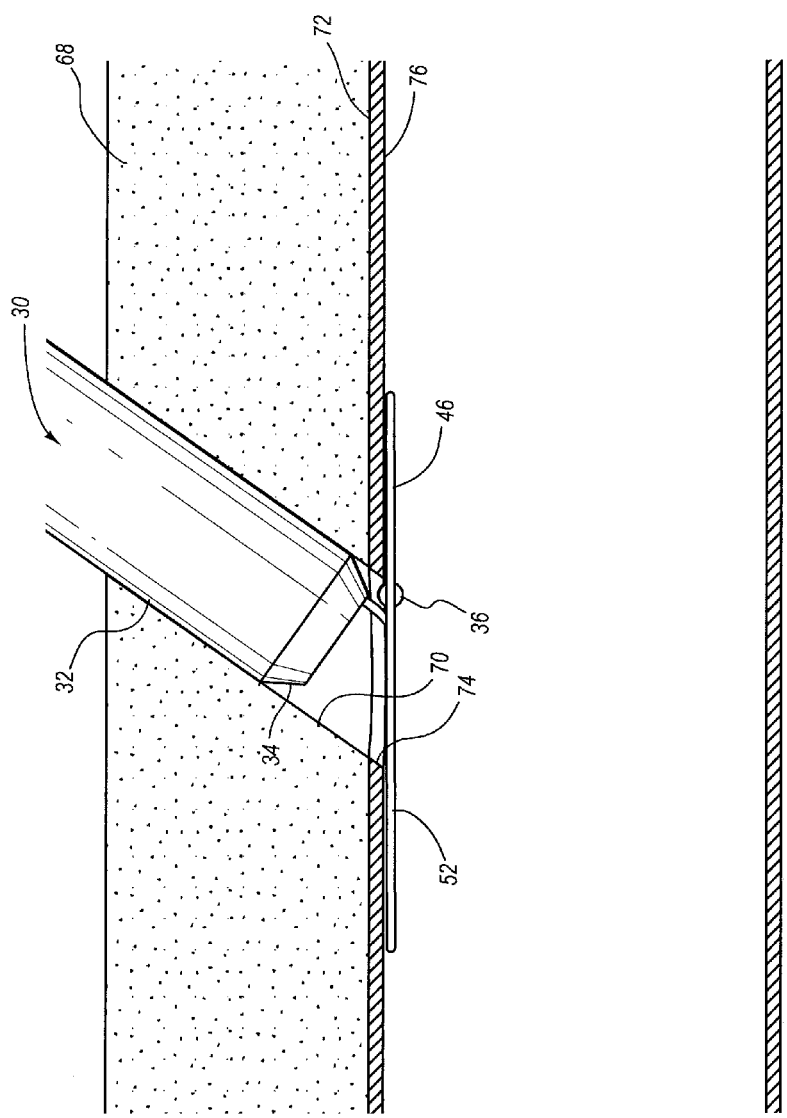
FIG. 11 is a side view of a vascular locator device disposed in a puncture tract according to an additional embodiment.

FIGS. 9-11 show vascular locator device 30 disposed in a puncture tract 70. As illustrated in FIG. 9, a distal portion of insertion sheath 32 of vascular locator device 30 may be inserted into and through puncture tract 70 defined within tissue 68 and/or vessel 72. Puncture tract 70 may include vessel puncture opening 74 formed in vessel 72. Distal end 33 of vascular locator device 30 may at least partially extend past interior vessel surface 76 of vessel 72 into an interior of vessel 72. One or more blood inlet holes (see, e.g., blood inlet hole 42 in FIG. 2) and/or any other suitable sensors and/or indicators may be used to indicate that vascular locator device 30 is inserted to an appropriate depth within puncture tract 70 and/or vessel 72. One or more blood inlet holes, indicators, and/or sensors may be employed to indicate over-insertion of vascular locator device 30 within puncture tract 70 and/or vessel 72.

At least a portion of locator wire 46 may be formed into an original and/or memorized shape prior to disposing locator wire 46 within at least a portion of insertion sheath 32. For example, distal locator portion 52 of locator wire 46 may be formed to any original shape suitable for use in locating at least a portion of a vessel and/or for positioning a vascular closure implant 45 within puncture tract 70. Distal locator portion 52 of locator wire 46 may retain shape memory of the original shape, even after being substantially distorted. In other words, distal locator portion 52 of locator wire 46 may retain the ability to return to the original shape, or substantially the original shape, even after being substantially distorted in shape by one or more external forces.

Following formation of distal locator portion 52 of locator wire 46 to an original shape and/or memorized shape, at least part of distal locator portion 52 may be formed to a distorted shape that is different from the original shape. For example, distal locator portion 52 of locator wire 46 may be formed to a distorted shape suitable for disposing distal locator portion 52 within insertion sheath 32, such as in locator passage 48 (see, e.g., FIG. 5). According to at least one embodiment, locator wire 46 may be substantially straightened within insertion sheath 32 under one or more external forces. Walls of locator passage 48 may maintain locator wire 46 in a distorted shape. Additionally, locator wire 46 may be formed to any distorted shape suitable for deploying locator wire 46 from vascular locator device 30 into puncture tract 70 and/or vessel 72. A shape of distal locator portion 52 within insertion sheath 32 may be referred to as an insertion shape configuration, since distal locator portion 52 is configured such that vascular locator device may be inserted into and through puncture tract 70.

FIG. 10 is a side view of an exemplary vascular locator device 30 at least partially disposed in a puncture tract 70. As illustrated in this figure, distal locator portion 52 of locator wire 46 may be deployed within vessel 72. Distal locator portion 52 of locator wire 46 may deploy using any suitable method for extending distal locator portion 52 to a position within vessel 72 external to insertion sheath 32. For example, following insertion and positioning of insertion sheath 32 within puncture tract 70 and/or vessel 72, as described above, an operator may apply a force to part of vascular locator device 30, such as, for example, button 40 on device handle 38 (see, e.g., FIG. 1), causing distal locator portion 52 of locator wire 46 to be removed from insertion sheath 32 to a position within vessel 72.

Upon or following removal from insertion sheath 32, distal locator portion 52 of locator wire 46 may assume a deployment shape configuration, as shown in FIG. 10. A shape of distal locator portion 52 when it is positioned outside of insertion sheath 32 may be referred to as a deployment shape configuration. The deployment shape configuration of distal locator portion 52 may the same or substantially similar to an original shape configuration assumed by distal locator portion 52 prior to positioning of distal locator portion 52 at least partially within insertion sheath 32 (see, e.g., the deployment configurations of distal locator portion 52 illustrated in FIGS. 6-8).

The deployment shape configuration of distal locator portion 52 of locator wire 46 may have a length wider than a width of insertion sheath 32, such as a width of a distal portion of insertion sheath 32. Accordingly, distal locator portion 52 may extend in a lateral direction past an outer diameter of insertion sheath 32. Additionally, as shown in FIG. 10, the deployment shape configuration of distal locator portion 52 of locator wire 46 may have a length greater than a diameter of vessel puncture opening 74 in vessel 72. Part of distal locator portion 52 of locator wire 46 may contact interior vessel surface 76 without damaging vessel 72. In at least one embodiment, part of distal locator portion 52 may bend or flex upon contact with interior vessel surface 76.

According to at least one embodiment, vascular locator device 30 may be positioned such that the lengthwise dimension of distal locator portion 52 of locator wire 46 is generally or substantially parallel to and/or in-line with the lengthwise dimension of vessel 72 when distal locator portion 52 is in a deployment shape configuration in vessel 72. In additional embodiments, locator wire 46 and/or vascular locator device 30 may be configured such that distal locator portion 52 may rotate following deployment in vessel 72, distal locator portion 52 rotating to a position where the lengthwise dimension of distal locator portion 52 of locator wire 46 is generally or substantially parallel to and/or in-line with the lengthwise dimension of vessel 72. Distal locator portion 52 may generally or substantially align with vessel 72 through various mechanisms. For example, a shape of distal locator portion 52 in the deployment shape configuration (see, e.g., FIGS. 6-8) may enable distal locator portion 52 to contact interior vessel surface 76 such that distal locator portion 52 rotates within vessel 72 until the lengthwise dimension of distal locator portion 52 of locator wire 46 is generally or substantially parallel to and/or in-line with the lengthwise dimension of vessel 72. According to certain embodiments, distal locator portion 52 may rotate within vessel 72 when force is applied to distal locator portion 52, such as when vascular locator device is retracted at least partially from vessel 72.

FIG. 11 is a side view of an exemplary vascular locator device 30 at least partially disposed in a puncture tract 70. As shown in this figure, vascular locator device 30 may be moved in a proximal direction, such that vascular locator device 30 is at least partially retracted from puncture tract 70. According to various embodiments, vascular locator device 30 may be retracted to a point where distal locator portion 52 of locator wire 46 is oriented adjacent or substantially adjacent to interior vessel surface 76. Distal locator portion 52 of locator wire 46 may be oriented such that it lies across vessel puncture opening 74. Additionally, distal locator portion 52 may contact parts of interior vessel surface 76 located on generally opposite sides of vessel puncture opening 74 in vessel 72. At least part of distal locator portion 52 may be positioned substantially flush with interior vessel surface 76. In addition, a portion of locator wire 46 may flex to allow distal locator portion 52 to pivot and orient relative to interior vessel surface. In at least one embodiment, distal locator portion 52 of locator wire 46 may pivot from the orientation in FIG. 10 to the orientation in FIG. 11. For example, distal locator portion 52 and/or curved portion 63 of locator wire 46 (see, e.g., FIG. 6) may flex to enable pivoting of distal locator portion 52. Additionally, part of distal locator portion 52 may flex to enable pivoting of distal locator portion 52.

According to at least one embodiment, distal locator portion 52 of locator wire 46 may at least partially conform to a shape of interior vessel surface 76 adjacent to distal locator portion 52. As described above, two or more of first curved segment 54, second curved segment 56, first intermediate segment 58, end segment 60, and transition segment 62 may be generally or substantially oriented in a common plane (see, e.g., FIGS. 6-8). In addition, the common plane may be oriented such that it generally faces and/or is generally or substantially parallel to interior vessel surface 76. According to at least one embodiment, vascular locator device 30 may be positioned such that the lengthwise dimension of distal locator portion 52 of locator wire 46 is generally or substantially parallel to and/or in-line with the lengthwise dimension of vessel 72 when distal locator portion 52 is in a deployment shape configuration in vessel 72.

The arrangement of distal locator portion 52 adjacent to interior vessel surface 76 may enable distal locator portion 52 to be positioned against interior vessel surface 76 while preventing damage to vessel 72 and/or tissue 68. According to various embodiments, locator wire 46 may have sufficient flexibility and resiliency to enable distal locator portion 52 to generally or substantially conform to a shape of interior vessel surface 76 adjacent to distal locator portion 52, thereby distributing forces applied by distal locator portion 52 to interior vessel surface 76. By conforming to a shape of interior vessel surface 76 and distributing forces applied by distal locator portion 52 to interior vessel surface 76, distal locator portion 52 may prevent injury to vessel 72 and/or tissue 68, and additionally, distal locator portion 52 may be held more securely in position against vessel 72.

According to various embodiments, once distal locator portion 52 contacts interior vessel surface 76 and/or generally or substantially conforms to a shape of interior vessel surface 76, as illustrated in FIG. 11, vascular locator device 30 may indicate to a user that vessel 72 has been located and/or that vascular locator device 30 is in position to perform a further procedure. A further procedure to be performed by a user of vascular locator device 30 may include, for example, insertion of a vascular closure implant 45 into puncture tract 70 and/or vessel puncture opening 74. In at least one embodiment, a user may rely on tactile feedback as vascular locator device 30 is being withdrawn to determine when vessel 72 has been located and/or that vascular locator device 30 is in position. According to additional embodiments, an indicator, such as, for example, a visual indicator may be located on a portion of vascular locator device 30 to indicate to a user that vessel 72 has been located and/or that vascular locator device 30 is in position.

After vessel 72 has been located using locator wire 46, distal locator portion 52 may be at least partially retracted into insertion sheath 32, and vascular locator device 30 may subsequently be removed from puncture tract 70. A force may be applied to locator wire 46 to retract distal locator portion 52 at least partially into insertion sheath 32, such as a force applied by a user of vascular locator device 30. For example, a user of vascular locator device 30 may apply a force to button 40 (see, e.g., FIG. 1) in a generally proximal direction, and button 40 may accordingly apply a force to locator wire 46 in a generally proximal direction, causing distal locator portion 52 to retract into insertion sheath 32. In at least one embodiment, distal locator portion 52 may be at least partially retracted into a locator passage 48 in a locator housing 50 (see, e.g., FIG. 5).

Locator wire 46 may take up a relatively small area in comparison with a vascular closure implant 45 that may also be disposed within insertion sheath 32. Additionally, locator wire 46 may be disposed to a side of vascular closure implant 45 within insertion sheath 32, lying between vascular closure implant 45 and insertion sheath 32. Accordingly, vascular closure implant 45 may be relatively easily disposed within and removed from insertion sheath cavity 44 without interference from locator wire 46. Additionally, although locator wire 46 may take up a relatively minimal space when retracted into insertion sheath 32, distal locator portion 52 of locator wire 46 may deploy into a relatively large deployment shape configuration that enables effective location of vessel 72 while allowing for distal locator portion 52 to be retracted back into insertion sheath 32.

FIG. 12 is a side view of a vascular locator device 30 disposed in a puncture tract 70. FIG. 13 is a perspective view of the distal locator portion 52 of the vascular locator device 30 shown in FIG. 12. As illustrated in these figures, distal locator portion 52 of vascular locator device 30 may conform generally or substantially to a shape of interior vessel surface 76. For example, a portion of vessel 72 may be curved, and likewise, a portion of interior vessel surface 76 may also be curved. Distal locator portion 52 may conform to the curved portion of interior vessel surface 76. As show in FIG. 12, distal locator portion 52 of locator wire 46 may flex along its length to conform to the curved portion of interior vessel surface 76, maintaining distal locator portion 52 in close proximity to interior vessel surface 76 and/or properly positioning vascular locator device 30 for deployment of a vascular closure implant 45. The ability of distal locator portion 52 to flex may ensure more accurate location of vessel 72 while minimizing potential injury or trauma to vessel 72. Distal locater portion 52 may flex in various ways to conform to various curves and/or undulations on interior vessel surface 76. Additionally, distal locator portion 52 may pivot with respect to insertion sheath 32 and/or elongated portion 53 of locator wire 46, enabling distal locator portion to more closely conform to interior vessel surface 76.

The preceding description has been provided to enable others skilled in the art to best utilize various aspects of the exemplary embodiments described herein. This exemplary description is not intended to be exhaustive or to be limited to any precise form disclosed. Many modifications and variations are possible without departing from the spirit and scope of the instant disclosure. It is desired that the embodiments described herein be considered in all respects illustrative and not restrictive and that reference be made to the appended claims and their equivalents for determining the scope of the instant disclosure.

Unless otherwise noted, the terms "a" or "an," as used in the specification and claims, are to be construed as meaning "at least one of." In addition, for ease of use, the words "including" and "having," as used in the specification and claims, are interchangeable with and have the same meaning as the word "comprising."

What is claimed is:

1. A vessel locator apparatus, comprising:
    a locator housing;
    an elongated cavity defined in the locator housing;
    an insertion sheath having an insertion sheath lumen and a central axis, the elongated cavity being arranged parallel to and laterally offset relative to the central axis, the insertion sheath and locator housing being integrally formed with each other; and
    a superelastic wire positioned at least partially in the elongated cavity, the superelastic wire having a proximal end and a distal end, the superelastic wire comprising:
        an elongated portion extending in a longitudinal direction;
        a distal locator portion having an original shape configuration comprising:
            a first curved segment;
            a second curved segment;
            a straight intermediate segment extending between the first curved segment and the second curved segment;
            a straight end segment extending between the second curved segment and the distal end of the superelastic wire, the end segment being parallel to the intermediate segment;
            a spherically rounded tip, the rounded tip protruding from the elongated cavity while the distal locator portion is in a vessel insertion configuration within the elongated cavity.

2. The vessel locator apparatus of claim 1, wherein the distal locator portion of the superelastic wire is positioned within the elongated cavity, wherein the distal locator portion has a distorted shape configuration differing from the original shape configuration while positioned in the elongated cavity.

3. The vessel locator apparatus of claim 2, wherein the distal locator portion is configured to automatically assume the original shape configuration after removal of at least part of the distal locator portion from the elongated cavity.

4. The vessel locator apparatus of claim 2, wherein the distal locator portion is not folded in the elongated cavity.

5. The vessel locator apparatus of claim 2, wherein the distal locator portion is straightened in the elongated cavity.

6. The vessel locator apparatus of claim 1, wherein the original shape configuration is a memorized shape configuration.

7. The vessel locator apparatus of claim 1, wherein the locator housing is positioned within the insertion sheath.

8. The vessel locator apparatus of claim 7, further comprising a vascular closure implant positioned within the insertion sheath adjacent the locator housing.

9. The vessel locator apparatus of claim 8, wherein the locator housing is positioned between the insertion sheath and an exterior of the vascular closure implant.

* * * * *